United States Patent [19]

Dietze et al.

[11] 4,150,121

[45] Apr. 17, 1979

[54] KININ CONTAINING INJECTION COMPOSITION

[75] Inventors: Günther Dietze; Matthias Wicklmayr, both of Munich, Fed. Rep. of Germany

[73] Assignee: THERA Gesellschaft für Patentverwertung mbH, Fed. Rep. of Germany

[21] Appl. No.: 864,472

[22] Filed: Dec. 27, 1977

[30] Foreign Application Priority Data

Dec. 27, 1976 [DE] Fed. Rep. of Germany ....... 2658984

[51] Int. Cl.$^2$ ...................... A61K 37/00; A61K 37/26
[52] U.S. Cl. ................................. 424/178; 424/177

[58] Field of Search ................................ 424/177, 178

[56] References Cited

U.S. PATENT DOCUMENTS 3,912,807  10/1975  Alburn et al. ........................ 424/178

*Primary Examiner*—Frederick E. Waddell
*Attorney, Agent, or Firm*—Burns, Doane, Swecker & Mathis

[57] ABSTRACT

There is disclosed an injection composition which is particularly useful for treating diabetes. This composition comprises from about 5 micrograms to about 1 milligram of at least one kinin per 40 units of insulin.

5 Claims, No Drawings

KININ CONTAINING INJECTION COMPOSITION

BACKGROUND OF THE INVENTION

1. Field of the Invention

This invention relates generally to injection compositions. More specifically, this invention relates to insulin containing injection compositions, which are especially useful for treating diabetes.

2. Description of the Prior Art

The increase in the blood sugar level, caused by diabetes mellitus due to the lowered endogenous production of insulin by the pancreas may be lowered to normal values by percutaneous, and especially intramuscular, injections of insulin obtained from animal pancreas secretions. In serious diabetes cases, it is often necessary to give the patient injections of insulin two or more times per day every day. Normally, patients are given 10 to 40 units in the morning and 4 to 20 units at night. However, these doses must often be increased substantially in order to maintain the blood sugar level at its normal physiologic value.

In order to attain a more lasting effect of one injection, the insulin is combined with substances which form salt-like or complex bonds with the insulin. It is known, for example, to combine insulin with protamine. The depo-effect so attained may be improved still further by the admixture of zinc ions. Such combination of the insulin with protamine, or possibly globulin, results in a delay of the resorption of the insulin from the point of injection into the organism in general, or the blood stream respectively, but an actual increase in its effect is not attained thereby. Furthermore, these known combinations will not neutralize the effects of non-tolerance as experienced by many patients when given a higher dosage of insulin, especially when treatments are given over long periods of time.

Insulin therapy has known side effects, including, among others, the hypoglycemia which leads to heavy outbreaks of perspiration, ravenous hunger, muscular contractions, etc., and also allergic reactions which often result in a resistance to insulin, thus necessitating the application of even heavier doses of insulin which in turn will intensify the side-reactions. In this connection, see Mehnert & Schoefflin, "Diabetologie in Klinik and Praxis", [Thieme, Stuttgart 1974] pp. 283 to 298.

The search has continued for improved insulin injection compositions which are particularly useful for treating diabetes. This invention was made as a result of that search.

OBJECTS AND SUMMARY OF THE INVENTION

Accordingly, a general object of the present invention is to avoid or substantially alleviate the above problems of the prior art.

A more specific object of the present invention is to provide an insulin containing injection composition.

Another object of the present invention is to provide an insulin containing injection composition which is especially useful for treating diabetes.

Other objects and advantages of the invention will become apparent from the following summary and description of the preferred embodiments of the present invention.

The present invention provides a kinin and insulin containing injection composition which is especially useful for treating diabetes. This solution comprises from about 5 micrograms to about 1 milligram of at least one kinin per 40 units of insulin.

DESCRIPTION OF THE PREFERRED EMBODIMENTS

It was found unexpectedly that a combination of insulin with at least one of the kinins, which are local tissue hormones, causes a significant increase in the effect of the insulin. According to the invention, an insulin dosage of 40 units should contain from about 5 micrograms to about 1 milligram of kinin in order to accomplish this intensification of the insulin effect.

These kinins are oligopeptides with 9 to 11 amino acid units. The nonapeptide Brady kinin with the amino acid sequence: ($NH_2$) arginine - proline - proline -glycine - phenylalanine - serine - proline - phenylalanine - arginine (COOH), and the decapeptide kallidin, extended at the amino end by an additional lysine residue, as well as the methlys-Bradykinin, extended by an additional methionine residue, are substances which, when applied even in minimum quantities have a kallikreine-like vasodilatoric effect on the circulation, will cause the relaxed muscular system to contract, and will also cause vehement local pain reactions when injected intra- and subcutaneously, even in minimum quantities. In this connection, see Werle, "Angewandte Chemie" 1961, pp. 689–720; "Arzneimittel", volume 1, Verlag Chemie 1968, pp. 876–80; and Lewis, Handbook of Experimental Pharmacology, volume XXV (Erdoes Springer-Verlag, New York, 1970), pp. 516–530.

It is also known that kinins, such as Brady kinin and kallidin, promote the mobility of the spermatozoa, and for this reason are recommended as means for increasing fertility, such as by artificial insemination. In this connection, see published German application No. 2,357,507.

Kinins are natural products resulting from the breaking up of certain proteins which are defined as kininogenes and which are generated by the fermentative effect of the kallikreine. Since their structure is now known, they can be synthesized without difficulty from the amino acids by chemical means.

The powerful intensifying effect of the kinins, when injected percutaneously together with the insulin, is surprising since, on the basis of previous tests, these substances would be expected to have somewhat of a bloodsugar-increasing effect because they promote the passage of the glucoses from the pulpy food in the small intestine into the circulating blood. In this connection, see Meng & Haberland "Kininogenases and Kallikrein", (Schattauer; New York, 1973), pp. 75–80; and Moriwaki et al "Kalinogenase and Kallikrein", (Schattauer; New York, 1975), pp. 57–62.

The good compatibility of the novel mixture is also surprising since intracutaneous injection of the Bradykinin or the kallidin causes vehement pain reactions even an amounts of about 0.1 microgram in 1 milliliter of solution. Although the composition comprising insulin and kinin contains a relatively large amount of kinin, i.e., from about 10 to about 1,000 micrograms in 1 milliliter of injection solution, such painful reactions are not observed in the usual subcutaneous injections.

Due to the decrease in the amount of insulin administered, the insulin level within the organism will be lowered, thus lessening the probability of an antibody formation, and thereby reducing the danger of insulin allergy, resistance or lipodystrophy. Furthermore, heretofore the insulin therapy could not take into account the diverse sensitivities of the muscular system and the liver to the insulin. Since the insulin threshold of the muscular system is relatively high, in order to insure the absorption of the glucose within the muscular tissue, it was necessary to apply dosages of insulin which were generally too strong for the liver.

The composition of the present invention comprising insulin combined with the kinin improves specifically the sensitiveness of the muscle to insulin, making it thus possible to control the insulin of the diabetic more efficiently by an injection containing a smaller number of insulin units, and thereby reducing the complications which arise in cases of serious diabetes mellitus such as blindness, arteriosclerosis, microangiopathy, kidney disease, etc., complications which may be prevented only by employing precise controls. The amount of kinin in the novel insulin preparation should generally be from about 5 micrograms to about 1 milligram, preferably from about 40 micrograms to about 500 micrograms, relative to a dosage of 40 units of insulin.

Since the kinins contain the amino acid serine and thus a hydroxyl group which may be esterified, they may be esterified with fatty acids, especially with medium and higher fatty acids which contain from about 12 to about 18 carbon atoms, such as palmitic or stearic acid. These esters are cleaved within the organism by the effect of the lipases, and the kinins are thereby released. In this manner it is possible to delay the kinin effect for the insulin preparation of the present invention. This will be particularly advantageous if the kinin derivative is combined with a depo-insulin. If this fatty acid ester of the kinins is used, it is possible to increase the dosage ten-fold if desired. In other words, the preparation to be injected may contain a dosage of from about 100 micrograms to about 10 milligrams of kinin ester per 40 units of insulin.

The present invention is further illustrated by the following examples. All parts and percentages in the examples as well as in the specification and claims are by weight unless otherwise specified.

EXAMPLE 1

One hundred milliliters of an "alt" insulin solution with 40 units of "Alt" insulin per milliliter are mixed with 20 milligrams of Brady kinin and are bottled in ampoules, each containing 10 milliliters of solution. The preparation is suitable for multiple subcutaneous or intramuscular injection.

EXAMPLE 2

One hundred milliliters of a suspension of insulin protaminate with 40 units of insulin per milliliter are mixed with 28 milligrams of Brady kinin and bottled in ampoules. The preparation is suitable for subcutaneous or intramuscular injection one to two times daily respectively.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in this art without departing from the spirit of the invention.

We claim:

1. A kinin and insulin containing injection composition comprising from about 5 micrograms to about 1 milligram of at least one kinin per 40 units of insulin.

2. The composition of claim 1 wherein said composition comprises from about 40 to about 500 micrograms of kinin per 40 units of insulin.

3. The composition of claim 1 wherein the kinin is selected from the group consisting of Brady kinin, kallidin, and mixtures thereof.

4. The composition of claim 2 wherein the kinin is selected from the group consisting of Brady kinin, kallidin, and mixtures thereof.

5. A depo-insulin composition which is suitable for application by injection, said composition comprising from about 0.1 to about 10 milligrams of a kinin selected from the group consisting of Brady kinin, kallidin, and mixtures thereof, said kinin being esterified with fatty acid, per 40 units of depot-insulin.

* * * * *